US00RE40119E

(19) United States
(12) Reissued Patent
Hodgen

(10) Patent Number: US RE40,119 E
(45) Date of Reissued Patent: Feb. 26, 2008

(54) ADJUNCTIVE THERAPY

(75) Inventor: Gary D. Hodgen, Virginia Beach, VA (US)

(73) Assignee: Eastern Virginia Medical School, Norfolk, VA (US)

(21) Appl. No.: 11/016,680

(22) Filed: Dec. 20, 2004

Related U.S. Patent Documents

Reissue of:
(64) Patent No.: 5,691,314
Issued: Nov. 25, 1997
Appl. No.: 08/617,048
Filed: Mar. 18, 1996

(51) Int. Cl.
*A61K 38/09* (2006.01)

(52) U.S. Cl. ..... 514/15; 514/800
(58) Field of Classification Search ..... None
See application file for complete search history.

(56) References Cited

U.S. PATENT DOCUMENTS

| | | | | | |
|---|---|---|---|---|---|
| 5,116,818 | A | * | 5/1992 | Hodgen et al. | 514/15 |
| 5,434,138 | A | * | 7/1995 | Konig et al. | 514/15 |
| 5,780,435 | A | | 7/1998 | Garnick et al. | 514/15 |
| 5,843,902 | A | | 12/1998 | Garnick et al. | 514/15 |
| 6,153,586 | A | | 11/2000 | Garnick et al. | 514/15 |
| 6,180,609 | B1 | | 1/2001 | Garnick et al. | 514/15 |
| 6,211,153 | B1 | | 4/2001 | Garnick et al. | 514/15 |
| 6,384,017 | B1 | | 5/2002 | Garnick et al. | 514/15 |

OTHER PUBLICATIONS

Diedrich et al. Suppression of the endogenous luteinizing hormone surge by the gonadotrophin–releasing hormone antagonist Cetrorelix during ovarian stimulation. Human Reproduction. 1994, vol. 9, No. 5, pp. 788–791.*

Ljungqvist et al. Antide and related antagonists of luteinizing hormone release with long action and oral activity. Proc. Natl. Acad. Sci. USA. Nov. 1988, vol. 85, pp. 8236–8240.*

Rivier et al. Gonadotrophin–Releasing Hormone Antagonists: Novel Members of the Azaline B Family. Journal of Medicinal Chemistry. 1995, vol. 38, No. 14, pp. 2649–2662.*

Lumsden et al., Treatment With the Gonadotropin Releasing Hormone–Agonist Goserelin. Brit. J. of Obstet. and Gyn. 1994. vol. 101, pp. 438–442.

Audebert et al., Deferred Versus Immediate Surgery For Uterine Fibroids. Brit. J. of Obstet. and Gyn. 1994. vol. 101, Suppl. 10, pp. 29–32.

Stovall et al, GnRH Agonist. Obstetrics and Gynecology. 1995, vol. 86, No. 1, pp. 65–71.

Soloway et al., Randomized Prospective Study. J. of Urol. 1995. vol. 154, pp. 424–428.

Perry et al., Goserelin. Drugs. 1996. vol. 51, No. 2, pp. 319–346.

Hellstrom et. al., A 3–Year Follow–Up of Patients. Brit. J. of. Urol. 1996. vol. 78, pp. 432–436.

* cited by examiner

*Primary Examiner*—Jeffrey Edwin Russel
(74) *Attorney, Agent, or Firm*—Dickstein Shapiro LLP

(57) ABSTRACT

A growth such as a tumor, hypertrophied tissue or cyst is biopsied or more completely excised subsequent to the administration of an effective amount of a gonadotropin releasing hormone analog or other inhibitor of ovarian steroid production or action.

19 Claims, No Drawings

ADJUNCTIVE THERAPY

Matter enclosed in heavy brackets [ ] appears in the original patent but forms no part of this reissue specification; matter printed in italics indicates the additions made by reissue.

BACKGROUND OF THE INVENTION

Almost 100 years ago it was recognized that breast cancer exhibited a degree of hormone dependency. Disease regression was achieved through estrogen ablation.

Studies of normal breast tissue indicate that endogenous hormones of the menstrual cycle influence rates of cell division and cell death. Speroff, The Breast, in: Speroff, Ed., Clinical Gynecologic Endocrinology & Infertility, Fourth Edition, Baltimore Williams & Williams: 1989: 629:91–119. Estrogen levels rise sharply and then fall in the absence of progesterone during the follicular phase of the cycle. Following ovulation, levels of these hormones increase and then decline before the onset of menses. The pattern of cyclic hormone concentration has been shown to influence both immune parameters and growth factors.

Laboratory studies have revealed that estrogen influences the growth fraction of human breast adenocarcinomics. When both estrogen and progesterone are present, this growth factor is significantly depressed. Jones, Influence of Steroid Hormones on the Growth Fraction of Human Breast Carcinomas, Am. J. Clin. Pathol. 1987, 88:132–138, Retardation of human breast cancer cells in the presence of progesterone has also been observed.

Cancer cells may be released into the circulation during surgery or other invasive procedures. It has therefore been suggested that a short, preoperative course of tamoxifen may be beneficial. McGuire, The Optical Timing of Mastectomy: Low Tide or High Tide?, Ann. Intern. Med. 1991, 115:401–403, Editorial. Some clinicians have proposed administering progesterone at the time of surgery to enhance prognosis by interrupting metastatic seeding.

The present invention contemplates the acute administration of a GnRH analog (or mime) as a pretreatment to invasive procedures such as surgery for breast, prostate or other cancers in order to decrease the reoccurrence rate. Administration results in the suppression of gonadal steroid dependent growth factors and neovascular processes that contribute to metastasis or recurrence in situ.

It is accordingly the object of the present invention to provide an adjunctive method to be employed in conjunction with the excisement of a neoplasm, cysts or portion thereof. This and other objects of the present invention will become apparent to those of ordinary skill in this from the following detailed description.

SUMMARY OF THE INVENTION

This invention relates to a therapy adjunctive to an invasive procedure and more particularly, to administering to a person prior to a procedure such as excising a growth or portion thereof, a gonadotropin releasing hormone analog or mime thereof and then conducting the procedure before the effect of the gonadotropin releasing hormone antagonist has dissipated.

DESCRIPTION OF THE INVENTION

In accordance with the present invention, the conventional invasive procedure for excising a growth (or portion thereof) is carried out but additionally, a gonadotropin releasing hormone analog or other inhibitor of ovarian steroidal supply impact ("mime") is administered before that procedure is effected.

The gonadotropin releasing hormone is a small polypeptide produced in the hypothalamus and is sometimes termed gonadotropic releasing hormone, luteinizing the hormone releasing hormone, GnRH or LHRH. Analogs in the form of antagonists and agonists are known and either can be used. The present invention preferably employs the gonadotropin releasing hormone antagonist. A GnRH antagonist acts by classical competitive receptor occupancy at the level of the GnRH receptor in the anterior pituitary. The effect is realized quickly and the more active antagonists can extinguish bioactive gonadotropin secretion within minutes, and in turn deplete gonadal estrogen, progesterone and androgen synthesis and secretion to castrate levels within the first day of treatment without a "flare effect" (stimulation of the receptor system), and in turn, without a delay in therapeutic benefit and without a transient exacerbation by temporary elevations of estrogen and androgen.

Examples of gonadotropin releasing hormone antagonists can be found, inter alia, in U.S. Pat. Nos. 4,409,208, 4,547,370, 4,565,804, 4,569,927, 4,619,914, and 5,198,533 and in WO 89/01944, the disclosures of which are incorporated herein by reference. Examples of such antagonists include Antide (a decapeptide represented by the formula D-Ac-D-2-Nal$^1$-DpClPhe$^2$-D-3-Pal$^3$-Ser$^4$-NiLys$^5$-D-NicLys$^6$-Leu$^7$-ILys$^8$-Pro$^9$-D-Ala$^{10}$), [Ac-D4ClDPhe$^1$, D4ClDPhe$^2$, DTrp$^3$, DArg$^6$, DAla$^{10}$] GnRH, [Ac-4ClDPhe$^2$, $D_3$Pal$^3$, Arg$^5$, $D_2$Nal$^6$, DAla$^{10}$] GnRH, [Ac-D2-Nal$^1$, 4ClDPhe$^2$, DTrp$^3$, DArg$^6$, DAla$^{10}$]GnRH, [Ac-$D_2$Nal$^1$, 4FDPhe$^2$, DTrp$^3$, DArg$^6$]GnRH, [Ac-D2Nal$^1$, 4-ClDPhe$^2$, DTrp$^3$, DhArg(Et$_2$)$^6$, DAla$^{10}$]GnRH, and [Ac-Nal$^1$, DME4ClPhe$^2$, DPal$^3$, Ser$^4$, Tyr$^5$, DArg$^6$, Leu$^7$, ILys$^8$, Pro$^9$, DAla$^{10}$] GnRH.

Further, a substitute for the gonadotropin releasing hormone antagonist or agonist can be employed. The inhibitors of steroid production or action are entities which mimic the activity of the antagonist sufficiently to reversibly inactivate gonadal response or impact of ovarian steroids, including the blockade of gonadotropin stimulated steroidogenesis. Examples include recombinant DNA derived gonadotropins, desialated gonadotropins whether natural or DNA derived, antibodies to gonadotropins, gonadotropic subunit parts, inhibitors of gonadotropin receptor activations (i.e., cell messengers), inhibin/activin and their analogs, and the like.

The gonadotropin releasing hormone antagonists or other inhibitors employed in the present invention can be administered in the form of pharmaceutically acceptable non-toxic salts or complexes. The salts include acid addition salts such as for instance hydrochloride, hydrobromide, sulfate, phosphate, nitrate, oxalate, fumarate, gluconate, tannate, maleate, acetate, benzoate, succinate, alginate, malate, ascorbate, tartrate and the like. The complexes can be with metals such as for example zinc, barium, calcium, magnesium, aluminum and the like.

Any known gonadotropin releasing hormone analog or other inhibitor can be employed. Also any mode of administration heretofore employed for such agents can also be employed in the practice of the present invention. Thus, the route of administration can be any conventional route where the analog is active, for instance orally, intravenously, subcutaneously, intramuscularly, sublingually, percutaneously, rectally, intranasally or intravaginally. Similarly, the administration form can be a tablet, dragee, capsule, pill, nasal mist, aerosol, solutions suspensions, suppositories and the like.

As a rule of thumb, the amount of gonadotropin releasing hormone analog or inhibitor administered is that sufficient to adjust the circulating estrogen to a value below about 20 pg/ml and preferably below about 10 pg/ml. Depending on the particular active agent employed, the dose administered is generally about 0.001 to 5 mg/kg of body weight, preferably about 0.05 to 5 mg/kg when administered intramuscularly. Also depending upon the particular agent employed, a single administration may suffice, although one or more additional administrations can be employed over a time period of about one week or up to 30 days, including daily, weekly or monthly. Since the effects of the administration last for several days, it is preferred that the initial gonadotropin releasing hormone antagonist or mime administration occur at least one day before the surgical procedure. The excising of the growth or a portion thereof (e.g. a biopsy) is carried out in conventional fashion before endogenous estrogen or progesterone production has been restored spontaneously and causes reversion to preadministration condition.

In order to demonstrate the present invention, an individual is administered the gonadotropin releasing hormone antagonist specified below intramuscularly or subcutaneously. One day later, a biopsy is effected. The antagonist and amount, which is administered after suspension in sesame oil, are:

| Analog or Mime | Dose mg/kg/day |
|---|---|
| Antide | 0.3 |
| Azaline B | 0.05 |
| [Ac-D4ClDPhe$^1$, D4ClDPhe$^2$, DTrp$^3$, DArg$^6$, DAla$^{10}$] GnRH | 0.5 |
| [Ac-4ClDPhe$^2$, $D_3$Pal$^3$, Arg$^5$, $D_2$Na]$^6$, DAla$^{10}$] GnRH | 0.5 |
| [Ac-D2-Nal$^1$, 4ClDPhe$^2$, DTrp$^3$, DArg$^6$, DAla$^{10}$] GnRH | 0.5 |
| [Ac-Nal$^1$, DME4ClPhe$^2$, DPal$^3$, Ser$^4$, Tyr$^5$, DArg$^6$, Leu$^7$, ILys$^8$, Pro$^9$, DAla$^{10}$] GnRH | 0.5 |

Application of the components, compositions and methods of this invention for the medical and/or pharmaceutical use which are described in this text may be accomplished by and clinical, medical or pharmaceutical methods or techniques as are presently or prospectively known to those skilled in the art. The various embodiments which have been described herein were intended to be representative and not limiting, as various changes and modifications can be made in the present invention without departing from the spirit and scope thereof.

What is claimed is:

1. A method which comprises administering to [an individual] *a person* an [effective] amount *effective to temporarily reduce circulating estrogen* of a gonadotropin releasing hormone antagonist or mime thereof *selected from the group consisting of antide and azaline B* and thereafter conducting an invasive procedure *to excise a growth or portion thereof* before the effect of the [analog] *antagonist* or mime thereof has dissipated.

[2. The method of claim 1 wherein the invasive procedure comprises excising a growth or portion thereof.]

3. The method of claim [2] *1* wherein the antagonist is administered about one day before the excisement.

4. The method of claim 3 in which only a single administration of the antagonist is effected.

[5. The method of claim 2 in which only a single administration of the antagonist is effected.]

[6. The method of claim 5 in which about 0.001 to 5 mg/kg of body weight of antagonist is administered.]

[7. The method of claim 2 in which about 0.5 to 5 mg/kg of body weight of antagonist is administered.]

8. The method of claim [2] *1* in which the antagonist is antide.

9. The method of claim [2] *1* in which the antagonist is azaline B.

[10. The method of claim 1 wherein the antagonist or mime is administered about one day before the invasive procedure.]

[11. The method of claim 10 in which only a single administration of the antagonist or mime is effected.]

12. The method of claim 1 in which only a single administration of the antagonist or mime is effected.

13. The method of claim 1 in which about 0.001 to 5 mg/kg of body weight of antagonist or mime is administrated.

14. The method of claim 1 in which about 0.5 to 5 mg/kg of body weight of antagonist or mime is administered.

*15. The method of claim 1 wherein the effective amount is that sufficient to adjust the circulating estrogen to a value below about 20 pg/ml.*

*16. The method of claim 1 wherein the effective amount is that sufficient to adjust the circulating estrogen to a value below about 10 pg/ml.*

*17. The method of claim 1 wherein the length of time of administration of the antagonist or mime thereof is about one week.*

*18. A method which comprises administering to a female person an effective amount of a gonadotropin releasing hormone antagonist or mime thereof, said antagonist or mime acting by competitive receptor occupancy, in an amount effective to adjust the circulating estrogen to a value below about 20 pg/ml, and thereafter conducting an invasive procedure which excises a tissue growth or portion thereof before the effect of the antagonist or mime thereof has dissipated and the circulating estrogen has a value above about 20 pg/ml.*

*19. The method of claim 18 wherein the effective amount is that sufficient to adjust the circulating estrogen to a value below about 10 pg/ml.*

*20. The method of claim 18 wherein the length of time of the antagonist or mime thereof administration is about one week.*

*21. The method of claim 18 wherein the antagonist is administered about one day before the excisement.*

*22. The method of claim 18 in which only a single administration of the antagonist is effected.*

*23. The method of claim 18 in which about 0.001 to 5 mg/kg of body weight of antagonist is administrated.*

*24. The method of claim 23 in which about 0.05 to 5 mg/kg of body weight of antagonist is administrated.*

*25. The method of claim 18 wherein the tissue growth or portion thereof excised is a tumor, hypertrophied tissue or a cyst.*

* * * * *